US009354235B2

(12) United States Patent
Roberts et al.

(10) Patent No.: US 9,354,235 B2
(45) Date of Patent: May 31, 2016

(54) SYSTEM AND PROCESS FOR QUANTIFYING POTENTIALLY MINERALIZABLE NITROGEN FOR AGRICULTURAL CROP PRODUCTION (71) Applicant: Board of Trustees of The University of Arkansas, Little Rock, AR (US)

(72) Inventors: Trenton L. Roberts, Fayetteville, AR (US); Richard J. Norman, Fayetteville, AR (US); Nathan A. Slayton, Springdale, AR (US); Charles E. Wilson, Jr., De Witt, AR (US)

(73) Assignee: Board of Trustees of The University of Arkansas, Little Rock, AR (US)

(*) Notice: Subject to any disclaimer, the term of this patent is extended or adjusted under 35 U.S.C. 154(b) by 96 days.

(21) Appl. No.: 14/209,245

(22) Filed: Mar. 13, 2014

(65) Prior Publication Data
US 2014/0273253 A1 Sep. 18, 2014

Related U.S. Application Data (60) Provisional application No. 61/786,899, filed on Mar. 15, 2013.

(51) Int. Cl.
*G01N 33/68* (2006.01)
*G01N 33/24* (2006.01)
*G01N 21/64* (2006.01)

(52) U.S. Cl.
CPC .......... *G01N 33/6809* (2013.01); *G01N 21/643* (2013.01); *G01N 33/24* (2013.01); *Y10T 436/143333* (2015.01); *Y10T 436/173845* (2015.01); *Y10T 436/176152* (2015.01)

(58) Field of Classification Search
CPC .............. G01N 33/68; G01N 33/6806; G01N 33/6809; G01N 33/24; G01N 21/64; G01N 21/643; Y10T 436/143333; Y10T 436/17; Y10T 436/173076; Y10T 436/173845; Y10T 436/176152; Y10T 436/255
USPC ........... 436/86, 89, 90, 94, 79, 106, 110, 111, 436/114, 164, 172, 178
See application file for complete search history.

(56) References Cited

U.S. PATENT DOCUMENTS

| 3,718,432 | A | 2/1973 | Roth |
| 4,670,403 | A | 6/1987 | Ishida et al. |
| 4,784,962 | A | 11/1988 | Apffel, Jr. et al. |
| 4,837,166 | A | 6/1989 | de Montigny et al. |
| 5,858,798 | A | 1/1999 | Godfrey et al. |
| 5,955,651 | A | 9/1999 | Coruzzi et al. |
| 6,699,709 | B1* | 3/2004 | Bonde ............ C12Q 1/34 435/262.5 |
| 2003/0077833 | A1* | 4/2003 | Campbell ........... G01N 33/493 436/90 |
| 2009/0011516 | A1 | 1/2009 | Loussaert et al. |
| 2011/0312100 | A1 | 12/2011 | Kampouris et al. |

FOREIGN PATENT DOCUMENTS

| CH | 508879 | 12/1976 |
| DE | 2659836 | 5/1976 |
| JP | 56129857 | 10/1981 |
| JP | 57135355 | 8/1982 |
| JP | 60253973 | 12/1985 |
| JP | 62209055 | 9/1987 |

OTHER PUBLICATIONS

Darrouzet-Nardi et al. Soil Biology & Biochemistry, vol. 57, Oct. 3, 2012, pp. 78-82.*
Roberts, T.L., W.J. Ross, R.J. Norman, N.A. Slaton, and C.E. Wilson Jr. 2011. Predicting Nitrogen Fertilizer Needs in Arkansas Using Alkaline Hydrolyzable-Nitrogen. Soil Sci. Soc. Am. J. 75:1161-1171.
Roberts, T.L., R.J. Norman, W.J. Ross, N.A. Slaton and C.E. Wilson Jr. 2012. Soil depth coupled with soil nitrogen and carbon can improve fertilization of rice in Arkansas. Soil Sci. Soc. Am. J. 76:2012.
Roberts, T.L., W.J. Ross, J.C. Stiegler, R.J. Norman, N.A. Slaton and C.E. Wilson Jr. 2012. Factors influencing the recovery of glucosamine nitrogen from soils commonly cropped to rice. Soil Sci. Soc. Am. J. 76:2012.
Roberts, T.L., R.J. Norman, N.A. Slaton, and C.E. Wilson Jr. 2009. Changes in alkaline hydrolyzable nitrogen distribution with soil depth: Implications for fertilizer correlation and calibration. Soil Sci. Soc. Am. J. 73:2143-2150.
Roberts, T.L., R.J. Norman, N.A. Slaton, C.E. Wilson Jr. W.J. Ross, and J.T. Bushong. 2009.Direct steam distillation as an alternative to the Illinois Soil Nitrogen Test. Soil Sci. Soc. Am. J. 73:1268-1275.
Bushong, J.T., T.L. Roberts, W.J. Ross, R.J. Norman, N.A. Slaton, and C.E. Wilson Jr. 2008. Evaluation of distillation and diffusion techniques for estimating hydrolyzable amino sugar-nitrogen as a means of predicting N mineralization. Soil Sci. Soc. Am. J. 72:992-999.

(Continued)

*Primary Examiner* — Maureen Wallenhorst
(74) *Attorney, Agent, or Firm* — Head, Johnson & Kachigian, P.C.

(57) ABSTRACT

The invention is generally directed to a system and process for fluorometrically quantifying potentially mineralizable nitrogen for agricultural crop production. The soil analysis process measures potentially mineralizable nitrogen and calibrates the application of soil-based nitrogen for site or field specific management of nitrogen fertilizers for crops grown on a wide variety of soil textures including sandy loam, silt loam and clay soils. The spectrofluorometric system and process may be utilized for routine soil testing with a lower sample to sample variability, and the automation of the spectrofluorometric system and process allows for simultaneous determination of potentially mineralizable soil organic nitrogen, ammonium and nitrate.

37 Claims, 5 Drawing Sheets

(56) References Cited

OTHER PUBLICATIONS

Khan, S.A., R.L. Mulvaney, and R.G. Hoeft. 2001. A simple soil test for detecting sites that are nonresponsive to nitrogen fertilization. Soil Sci. Soc. Am. J. 65:1751-1760.

Mulvaney, R. L., S. A. Khan, and T. R. Ellsworth. 2006. Need for a soil-based approach in managing nitrogen fertilizers for profitable corn production. Soil Sci. Soc. Am. J. 70:172-182.

Spargo, J.T., M.M. Alley, W.E. Thomason, and S.M. Nagle. 2009. Illinois soil nitrogen test for prediction of fertilizer nitrogen needs of corn in Virginia. Soil Sci. Soc. Am. J. 73:434-442.

Williams, J.D., C.R. Crozier, J.G. White, R.P. Sripada, and D.A. Crouse. 2007a. Comparison of soil nitrogen tests for corn fertilizer recommendations in the humid Southeastern USA. Soil Sci. Soc. Am. J. 71:171-180.

Williams, J.D., C.R. Crozier, J.G. White, R.W. Heiniger, R.P. Sripada, and D.A. Crouse. 2007b. Illinois Soil Nitrogen Test predicts Southeastern U.S. corn economic optimum nitrogen rates. Soil Sci. Soc. Am J. 71:735-744.

Barker, D.W., J.E. Sawyer, and M.M. Al-Kaisi. 2006a. Assessment of the amino sugar-nitrogen test on Iowa soils: I. Evaluation of soil sampling and corn management practices. Agron. J. 98:1345-1351.

Barker, D.W., J.E. Sawyer, M.M. Al-Kaisi, and J.P. Lundvall. 2006b. Assessment of the amino sugar-nitrogen test on Iowa soils: II. Field correlation and calibration. Agron. J. 98:1352-1358.

Klapwyk, J.H., and Q.M. Ketterings. 2006. Soil tests for predicting corn response to nitrogen fertilizer response in New York. Agron. J. 98:675-681.

Laboski, C.A.M., J.E. Sawyer, D.T. Walters, L.G. Bundy, R.G. Hoeft, G.W. Randall, and T.W. Andraski. 2008. Evaluation of the Illinois soil nitrogen test in the North Central region of the United States. Agron. J. 100:1070-1076.

Osterhaus, J.T., L.G. Bundy, and T.W. Andraski. 2008. Evaluation of the Illinois soil nitrogen test in Wisconsin cropping systems. Soil Sci. Soc. Am. J. 72:143-150.

Wilson, C.E., Jr., R.J. Norman, B.R. Wells, and M.D. Correll. 1994a. Chemical estimation of nitrogen mineralization in paddy rice soils: I. Comparison to laboratory indices. Commun. Soil Sci. Plant Anal. 25:573-590.

Wilson, C.E., Jr., R.J. Norman, B.R. Wells, and M.D. Correll. 1994b. Chemical estimation of nitrogen mineralization in paddy rice soils: II. Comparison to greenhouse availability indices. Commun. Soil Sci. Plant Anal. 25:591-604.

Sims, J.L., J.P. Wells, and D.L. Tackett. 1967. Predicting nitrogen availability to rice: I. Comparison of methods for determining available nitrogen to rice from field and reservoir soils. Soil Sci. Soc. Am. Proc. 31:672-675.

Smith, J.A. 1966. An evaluation of nitrogen soil test methods for Ontario Soils. Can. J. Soil Sci. 46:185-194.

Stanford, G. 1982. Assessment of soil nitrogen availability. In F.J. Stevenson et al. (ed.) Nitrogen in agricultural soils. Agronomy 22:651-688.

Stanford, G., and S.J. Smith. 1978. Oxidative release of potentially mineralizable soil nitrogen by acid permanganate extraction. Soil Sci. 126:210-218.

Mulvaney, R.L., S.A. Khan, R.G. Hoeft, and H.M. Brown. 2001b. A soil organic nitrogen fraction that reduces the need for nitrogen fertilization. Soil Sci. Soc. Am. J. 65:1164-1172.

Jones, D.L., A.G. Owen, and J.F. Farrar. 2002. Simple method to enable high resolution determination of total free amino acids in soil solutions and soil extracts. Soil Biology and Biochemistry 34:1893-1902.

Magdoff, F.R., D. Ross, and J. Amadon. 1984. A soil test for nitrogen availability to corn. Soil Sci. Soc. Am. J. 48:1301-1304.

Magdoff. F. 1991. Understanding the Magdoff pre-sidedress nitrate test for corn. J. Prod. Agric. 4:297-305.

Meisinger, J.J., V.A. Bandel, J.S. Angle, B.E. O'Keefe, and C.M. Reynolds. 1992. Presidedress soil nitrate test evaluation in Maryland. Soil Sci. Soc. Am. J. 56:1527-1532.

Fox, R.H. and W.P. Piekielek. 1978. Field testing of several nitrogen availability indexes. Soil Sci. Soc. Am. J. 42:747-750.

Fox, R.H., G.W. Roth, K.V. Iversen, and W.P. Piekielek. 1989. Soil and tissue nitrate tests compared for predicting soil nitrogen availability to corn. Agron. J. 81:971-974.

Keeney, D.R. 1982. Nitrogen-availability indices. In A.L. Page et al. (ed.) Methods of soil analysis. Agronomy 9:711-733.

Keeney, Dr., and J.M. Bremner. 1964. Effect of cultivation on the nitrogen distribution in soils. Soil Sci. Soc. Am. Proc. 28:653-656.

http://www.sciencedirect.com/science/article/pii/S0038071712002921 OPAME and standard fluorescence curve included in abstract and paper summary.

http://www.sciencedirect.com/science/article/pii/S0039914004005028 Includes calibration curve data.

http://www.hse.niordc.ir/uploads%5C86_106_Binder4.pdf Section 50.5; see also p. 65, Section 50.5.4.

http://onlinelibrary.wiley.com/doi/10.1002/jpln.200321302/pdf Automated fluorescence detection of glucosamine, galactosamine, muramic acid and mannosamine in soil using OPA.

https://www.soils.org/publications/sssaj/abstracts/52/4/SS0520040969.

http://pubs.acs.org/doi/abs/10.1021/ac00153a016.

http://pubs.acs.org/doi/abs/10.1021/jf00091a027.

http://www.sciencedirect.com/science/article/pii/S0039914001003587.

\* cited by examiner

SYSTEM AND PROCESS FOR QUANTIFYING POTENTIALLY MINERALIZABLE NITROGEN FOR AGRICULTURAL CROP PRODUCTION

CROSS REFERENCE TO RELATED APPLICATIONS

This application claims the benefit of U.S. Provisional Patent Application No. 61/786,899, filed Mar. 15, 2013, which is incorporated herein by reference.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

REFERENCE TO A SEQUENCE LISTING, A TABLE, OR A COMPUTER PROGRAM LISTING APPENDIX

Not applicable.

BACKGROUND OF THE INVENTION

1. Field of the Invention

This invention relates generally to a system and process for fluorometrically quantifying potentially mineralizable nitrogen for agricultural crop production, and in particular to a process of soil analysis for measuring potentially mineralizable nitrogen and calibration of the soil-based nitrogen process to allow for site or field specific management of nitrogen fertilizers.

2. Description of the Related Art

For field crops within the United States there is currently no analytical method used on a state or regional basis that can consistently and accurately predict the amount of soil nitrogen mineralized during a cropping season, and in turn the nitrogen fertilizer needs required for achieving optimum yields on a site-specific or year to year basis. Current nitrogen fertilizer recommendations for rice, wheat, corn, grain sorghum and cotton in the U.S. are typically based on soil texture, variety, yield goal and/or the previous crop grown. This approach often will maximize yields, but in many cases leads to over-fertilization with nitrogen resulting in increased lodging potential as well as requiring additional input costs in the form of fungicides to reduce disease pressure.

As such, management of fertilizer nitrogen is a critical component for producing consistent crop yields, as nitrogen fertilizer represents a considerable input cost and has serious environmental consequences if over applied. For example, nitrogen fertilizer costs represent anywhere from 20-30% of a producer's total input expenditures for rice produced on silt loam soils. The prevalence of nitrogen in the cells of agronomic crops means that harvest removes large quantities of nitrogen from a field, and, in doing so, creates a paucity of the nutrient residual in the soil for future production. This, coupled with nitrogen loss from soils by leaching, volatilization and denitrification, establishes a situation in which nitrogen is the nutritional factor most commonly limiting crop yield potential. To remedy this, plant-available nitrogen forms are provided to the crop in the form of chemical fertilizers, such as anhydrous ammonia and urea. Synthetic nitrogen fertilization is a cornerstone of modern agriculture because it provides the nutrients needed for elevated grain yield and quality. Therefore, it is important to apply the correct amount of fertilizer to meet the crop's need but not to supply more than is required because of the cost and environmental concerns.

The diagnosis of in-season nitrogen deficiencies must be followed by corrective nitrogen applications to recover potential yield. A key to corrective nitrogen fertilization action is up-to-date knowledge of advent and degree of nitrogen deficiency. Immediate knowledge of plant nitrogen concentration is often not obtainable due to a lag time for processing. This lag time can negatively affect the value of the derived information due to the short window during which nitrogen demand is increasing and deficiencies can be most effectively corrected.

There are few tools that are currently available to help farmers determine if crop nitrogen levels during the season are adequate, and several techniques have been used to objectively measure crop color, including reflectance measurements, chlorophyll and amino acid analysis. Reflectance, chlorophyll, and amino acid measurements all require relatively expensive equipment, and transport of samples to a laboratory for analysis. Shipping these materials to a qualified testing service can compromise the brief window in which the information might be of value.

It is therefore desirable to provide a system and process for fluorometrically quantifying potentially mineralizable nitrogen for agricultural crop production.

It is further desirable to provide a process soil analysis for measuring potentially mineralizable nitrogen and calibration of the soil-based nitrogen process to allow for site or field specific management of nitrogen fertilizers.

It is yet further desirable to provide a soil analysis process that allows producers to utilize field-specific nitrogen rates rather than applying blanket recommendations based on rice variety, soil texture, and previous crop.

It is still further desirable to provide a system and process for fluorometrically quantifying potentially mineralizable nitrogen for agricultural crop production that is automated, faster, less laborious, uses less caustic chemicals and is more apt to be used in mainstream soil test laboratories and adapted on a wide scale than prior methods.

It is yet further desirable to provide an automated fluorometric soil analysis system and process that provides savings due to a reduction in nitrogen fertilizer needs, while still maximizing yields, and savings in fungicide costs due to less disease incidence and/or severity of disease.

It is still further desirable to provide a system and process for fluorometrically quantifying potentially mineralizable nitrogen for agricultural crop production that increases yield due to a reduction in the incidences and severity of lodging, and that increases earnings from increased yields on fields that have unknowingly been under fertilized with nitrogen fertilizer.

BRIEF SUMMARY OF THE INVENTION

In general, the invention relates to a process for quantifying potentially mineralizable nitrogen for agricultural crop production. The process includes fluorometrically quantifying at least one amino acid or amino sugar content having an exposed amine group from an agricultural crop soil sample using a salt solution; and predicting potentially mineralizable soil nitrogen content based on the quantification. The salt solution is potassium chloride, potassium sulfate, calcium sulfate or calcium chloride, namely 2M KCL at an aliquot volume range between about 20 μL and about 100 μL. The salt solution to crop soil sample ratio can be between the range of about 1:1 to about 30:1. The process can be utilized on a variety of soil textures including, but not limited to sandy loam, silt loam or clay soil and agricultural crops, such as rice, corn, grain sorghum, cotton, wheat, pastures or hay. In addition, the inventive process can include predicting at least about 90% of a maximum potential yield of the crop.

Further, the process can include using a reagent of o-phthaldialdehyde or β-mercaptoethanol or a thiol reagent, such as ethanethiol, 3-mercaptopropionic acid or N-acetyl-L-cysteine. Moreover, the amino acid or amino sugar content can be a total amino acid, amino sugar, urea and/or uric acid content having an exposed amine groups, such as asparagine, arginine, glutamine, glycine, lysine, glucosamine, mannosamine and galactosamine, but excludes unexposed amine groups, such as proline and/or N-acetyl-glucosamine.

Other advantages and features of the invention will be apparent from the following description and from the claims.

DETAILED DESCRIPTION OF THE INVENTION

The processes and systems discussed herein are merely illustrative of specific manners in which to make and use this invention and are not to be interpreted as limiting in scope.

While the processes and systems have been described with a certain degree of particularity, it is to be noted that many variations and modifications may be made in the details of the sequence and the arrangement of the processes and systems without departing from the scope of this disclosure. It is understood that the processes and systems are not limited to the embodiments set forth herein for purposes of exemplification.

The invention relates to a system and process for fluorometrically quantifying potentially mineralizable nitrogen for agricultural crop production. The system and process for soil analysis measure potentially mineralizable nitrogen and provide calibration of the application of soil-based nitrogen to allow for site or field specific management of nitrogen fertilizers. The system and process allows producers to utilize field-specific nitrogen rates rather than applying blanket recommendations based on crop variety, soil texture, and previous crop, and is automated, faster, less laborious, uses less caustic chemicals and is more apt to be used in mainstream soil test laboratories and adapted on a wide scale than prior methods. Moreover, system and process for soil analysis fluorometrically quantify at least one amino acid or amino sugar content having an exposed amine group, and can quantify a total amino acid, amino sugar, urea and/or uric acid content. The system and process for fluorometrically quantifying potentially mineralizable nitrogen disclosed herein can be utilized with any amino acid having an exposed amine group, such as asparagine, arginine, aspartate, glutamate, glutamine, glycine, histidine, lysine, glucosamine, mannosamine and galactosamine, but not with amino acids having an unexposed amine group, namely proline and/or N-acetyl-glucosamine.

The system and process determines and quantifies a soil's nitrogen mineralization potential using spectrofluorometric detection, which is highly correlated with alkaline hydrolyzable-nitrogen. The system and process uses molecular fluorescence to predict either potentially mineralizable nitrogen or alkaline hydrolyzable-nitrogen for an agricultural crop, such as rice, corn, grain sorghum, cotton, wheat, pastures, hay or any other crop grown in soils that requires nitrogen fertilization. In addition, the system and process uses a salt extraction procedure that can be adapted to a wide variety of salt solutions and soil types. Moreover, the system and process for fluorometrically quantifying potentially mineralizable nitrogen for agricultural crop production provides calibration curves in order to accurately predict nitrogen fertilizer needs on a field-to-field basis.

The systems and process are also directed to a predictive tool for determining nitrogen fertilizer requirements from spectrofluorometric measurements. For example, the systems and process may utilize the soil's measured spectrofluorometric values to predict the amount of nitrogen fertilizer that should be applied to recover a predetermined crop yield potential, such as 90 to 100% of the maximum potential yield.

EXAMPLES

The system and process for fluorometrically quantifying potentially mineralizable nitrogen for agricultural crop production disclosed herein is further illustrated by the following examples, which are provided for the purpose of demonstration rather than limitation. Although the system and process were used with rice produced on silt loam soils in the following examples, any crop requiring nitrogen fertilization can be used.

Twenty five nitrogen response trials were conducted on experiment stations and producer fields from 2004-2008 to determine the optimum nitrogen rate for direct-seeded, delayed-flood rice on silt loam soils in the primary rice producing regions of Arkansas. Soil samples were collected prior to the application of pre-flood nitrogen from four test plots of rice. A minimum of four soil cores from each test plot were taken to a depth of 45 cm and combined to form a composite for each test plot. Samples were dried within 24 hours of collection at 40° C. and ground to pass through a 2-mm sieve and stored for further analysis.

The system and process for quantifying potentially mineralizable nitrogen for agricultural crop production can utilize varying salts to effectively extract from the soil inorganic nitrogen and organic nitrogen compounds that contribute to soil nitrogen mineralization. Salts that are effective in this extraction process include but are not limited to potassium chloride and calcium chloride, and the process can be modified to use distilled water, deionized water or other salt solutions as needed. Potassium chloride is used in routine soil testing to quantitatively extract inorganic nitrogen in the form of ammonium and nitrate, and the system and process provided herein uses potassium chloride to effectively extract organic nitrogen compounds associated with potentially mineralizable soil nitrogen.

The various extractant solutions were compared over a range of extractant to soil ratios including 1:1 5:1 10:120:1 and 30:1 (extractant:soil) and all dilutions worked equally well in quantifying ammonium, amino acids and amino sugars. Following extraction, solutions were subjected to the spectrofluorometric process that allows for direct quantification of ammonium, amino acids, urea and amino sugars. Under the spectrofluorometric process, a reagent utilizes a spectrofluorometric protocol including o-phthaldialdehyde and β-mercaptoethanol (OPAME) which is used in the detection of amino acids using HPLC and is much more sensitive than the ninhydrin method commonly used in the quantification of amino acids. Varying thiol reagents can be used in place of β-mercaptoethanol including ethanethiol, 3-mercaptopropionic acid and N-acetyl-L-cysteine. Sample aliquot size can vary based on the detection level that is desired as well as the concentration of nitrogen in the soil extracts, but a wide range of sample volumes has been tested and 20 μL appears to capture a wide range of nitrogen concentrations while still providing a relatively low and repeatable level of quantification.

The amount of nitrogen quantified by the spectrofluorometric process was then correlated with nitrogen mineralization potential and serves as an index of the potentially mineralizable nitrogen in the soil. This index was then correlated with crop response parameters such as total nitrogen uptake and percent relative grain yield. A series of experiments were then completed to identify the organic and inorganic nitrogen compounds that were extracted and quantified using the system and process disclosed herein.

Compounds of interest for soil fertility professionals that are accurately quantified using the system and process disclosed herein are glucosamine, mannosamine, glycine, alanine, glutamine, asparagine and ammonium. In addition, the system and process disclosed herein is further useful as it has the ability to quantify all free amino acids except proline and all amino sugars except N-acetyl-glucosamine. The use of a salt extract such as potassium chloride allows for simultaneous determination of nitrate, which is useful in upland crops, such as corn, grain sorghum, wheat and cotton. The system and process disclosed herein may be automated using an autoanalyzer retrofitted with a spectrofluorometer. Moreover, the system and process disclosed herein allows for simultaneous determination of amino acids, amino sugars, urea, ammonium and nitrate.

Example 1

Calibration Curves of Pure Amino Acids and Amino Sugars

A split-plot design was utilized with product being the main plot and rate being the sub-plot was replicated three (3) times. The products in this example were amino acids arginine, asparagine, glutamine, glycine, lysine and proline, and the amino sugars were glucosamine, mannosamine, galactosamine and N-Acetyl-Glucosamine. The experiment included concentrations of varying magnitudes, namely between 0, 5, 10, 25, 50 and 100 μM. The results of Example 1 are illustrated in FIGS. 1 through 4, which highlight that the system and process disclosed herein quantifies the compounds that are important for nitrogen mineralization in the soil. In addition, the system and process disclosed herein can provide an estimate of potentially mineralizable nitrogen. These results from Example 1 show that the flourescent system and process is accurate in quatifying the concentration of amino acids and amino sugars in a KCl matrix. The system and process acurately quanitifles the amino acids that are potentially mineralizable (e.g., glycine, gluatimine arginine and asparagine) and does not quanitfy amino acids such as proline that do not breakdown in the soil effectively and provide nitrogen. The same is true for the amino sugar compounds, the system and process acurately quanitifies the amino sugars that are relevant for nitrogen mineralization (e.g., glucosamine, mannosamine, galactosamine) but does not quanitfy N-acetyl-glucosamine, which is significantly less available for nitrogen mineralization.

Based on these results, the system and process disclosed herein accurately quantifies amino acids and amino sugars in a KCl salt solution (salt extractant) that have exposed amine groups, such as arginine, glutamine, glycine, lysine etc., but does not quanitfy amino acids and amino sugars, such as proline and N-acetyl-glucosamine, which do not have exposed amine groups. The concetration ranges for these amino acids and amino sugars widely vary using the system and process and are dependent of detector settings and dilution ratios.

Example 2

Standard Addition of $NH_4^+$ to Determine Level of Interference

In this example, a full factorial design was utilized for the products of glycine, glutamine, glucosamine and galactosamine, with four (4) different ammonium ($NH_4^+$) concentrations replicated three (3) times. The ammonium concentrations for this example varied between 0, 250, 500, 750 and 1000 μM. These concentrations include common $NH_4^+$ that might be found in agricultural soils within the United States.

Figure 1:
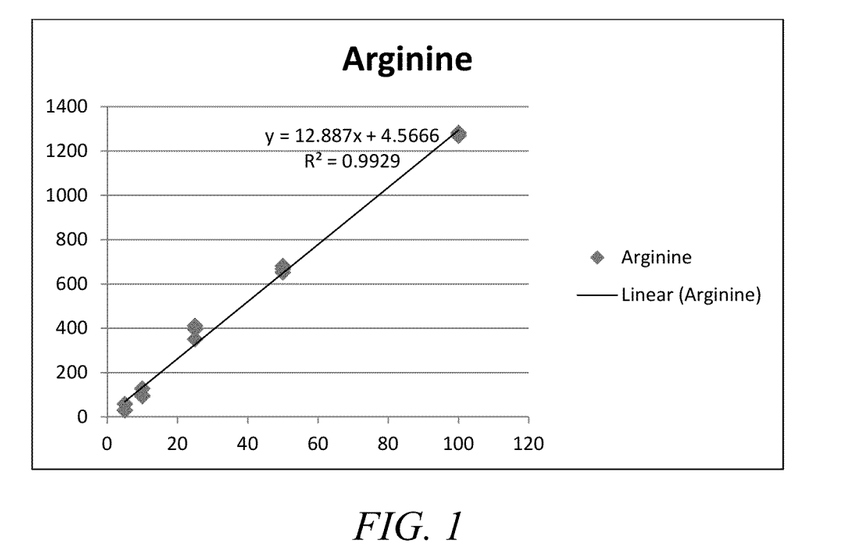
FIG. 1 graphically illustrates the relationship between arginine concentration (X-axis) and relative fluorescence units (RFU) (Y-axis) in accordance with Example 1 of the system and method for quantifying potentially mineralizable nitrogen for agricultural crop production disclosed herein.
Figure 2:
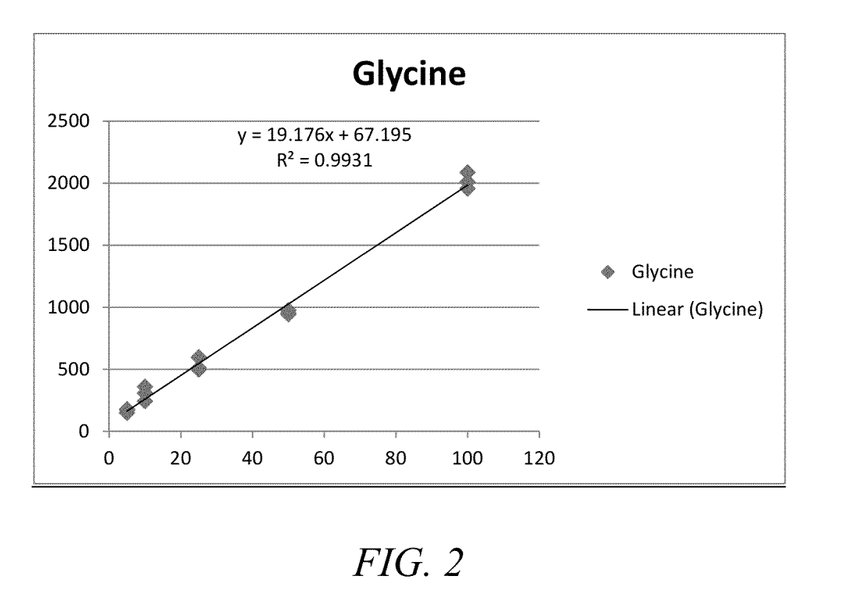
FIG. 2 graphically illustrates the relationship between glycine concentration (X-axis) and RFU (Y-axis) in accordance with Example 1 of the system and method for quantifying potentially mineralizable nitrogen for agricultural crop production disclosed herein.
Figure 3:
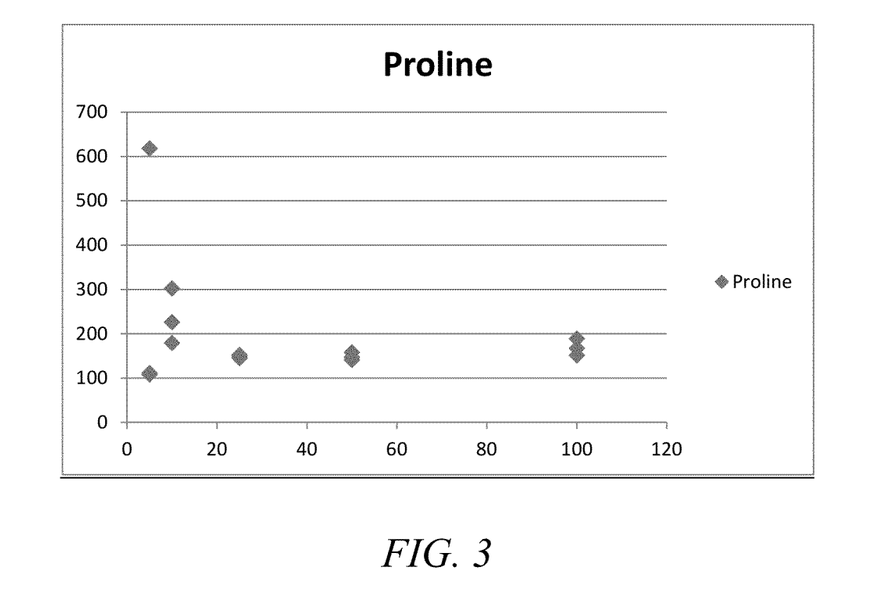
FIG. 3 graphically illustrates the relationship between proline concentration (X-axis) and RFU (Y-axis)
Figure 4:
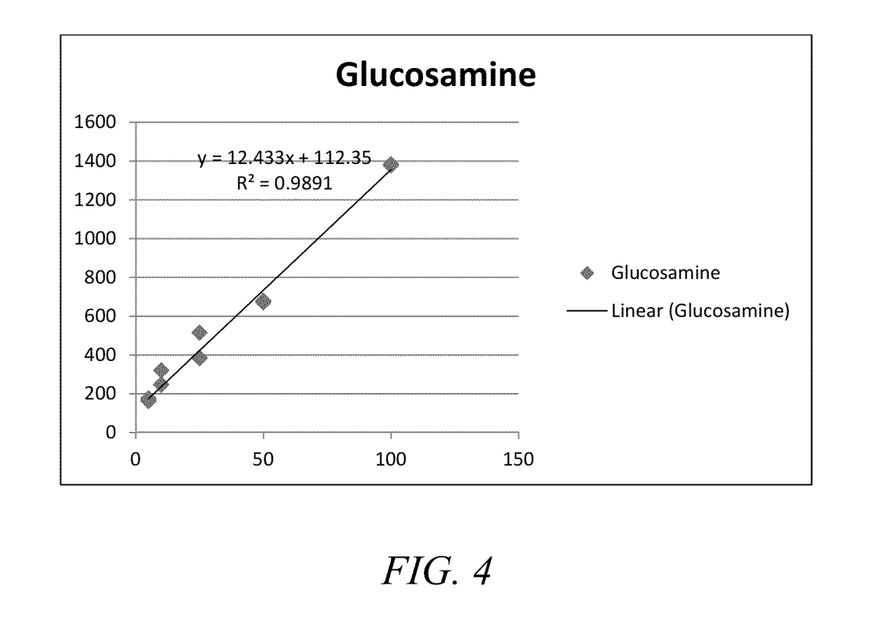
FIG. 4 graphically illustrates the relationship between glucosamine concentration (X-axis) and RFU (Y-axis) in accordance with Example 1 of the system and method for quantifying potentially mineralizable nitrogen for agricultural crop production disclosed herein.
Figure 5:
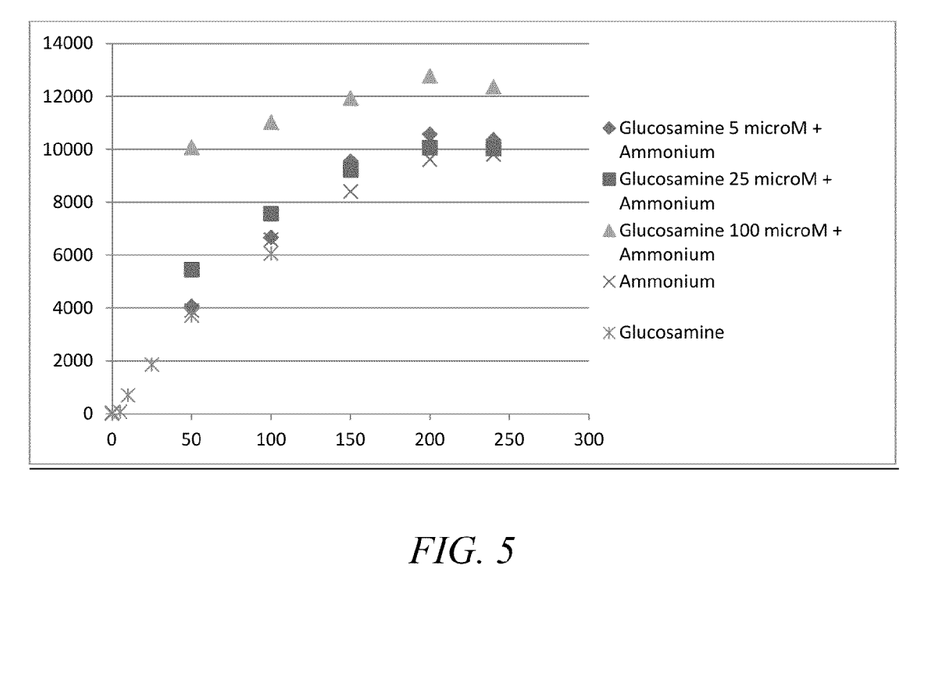
FIG. 5 graphically illustrates the relationship between ammonium and glucosamine concentration (X-axis) in solution and the resultant effect on RFU (Y-axis) in accordance with Example 2 of the system and method for quantifying potentially mineralizable nitrogen for agricultural crop production disclosed herein.

As illustrated in FIG. 5, when a known amount of ammonium was added to a known amount of amino acid or amino sugar, the RFU from the combination should be equal to the sum of the individual RFU units. This demonstrates that the influence of measuring these two compounds simultaneously is an additive effect and that there is no need to make any adjustments for calibration using the system and process for quantifying potentially mineralizable nitrogen for agricultural crop production.

The results of this experiment indicate that the system and process disclosed herein accurately quanitifies both amino acids and amino sugars in combination with ammonium in KCl extracts. As such, the system and process provide a simple additive effect, and the calibration curves for all three (3) types of compounds can be the same and that there is no need to create a corection factor to account for the amount of ammoium contained in the sample when the system and process for quantifying potentially mineralizable nitrogen for an agricultural crop production is utilized. These results also indicate that the relationship between RFU and nitrogen is linear, and as the amount of nitrogen in an extract increases, the RFUs increase linearly until the saturation point is reached.

Based on the foregoing results, the system and method quantifies amino acids, amino sugars and ammonium equally, and when utilizing the system and process, there is no need to correct the values for ammonium content. As demonstrated, there is no interference in the system and process due to the presence of ammonium and the nitrogen that it contains is quantified just the same as amino acids and amino sugars.

Example 3

Evaluation of Aliquot Volume on Quantification of Free Amino Acids and Amino Sugars in a 2M KCl Soil Extract In this experiment, a full factorial design with eight (8) soils and (5) aliquot volumes were replicated (3) times. Soils had a wide range of both total nitrogen (TN) and total carbon (TC) values with similar concentrations of inorganic nitrogen. In this experiment, aliquot volumes varied between 20, 60, 80, 100 µL of 10:1 2M KCl extract. A 10:1 KCl:soil ratio was chosen for this example because it is a commonly used extraction ratio and would introduce the least potential for background or matrix interference.

Figure 6:
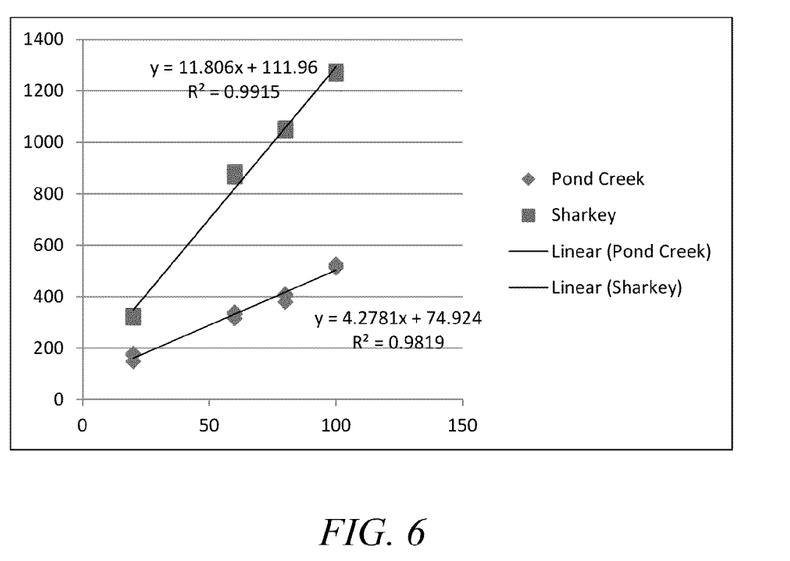
FIG. 6 graphically illustrates the relationship between aliquot volume (μL) (X-axis) for various soils and the resultant effect on RFU (Y-axis) in accordance with Example 3 of the system and method for quantifying potentially mineralizable nitrogen for agricultural crop production disclosed herein.

As illustrated in FIG. 6, as the aliquot volume was changed, the amount of nitrogen contained in the sample was changed. Correspondingly, as the amount of nitrogen increases (with increasing aliquot volume), within a specific soil series there is a very strong linear relationship between aliquot volume and RFU indicating that the calibration curves discussed below can be utilized over a wide range of aliquot volumes. In addition, the results of this experiment indicate that this method can accurately quanitify amino acids, amino sugars and ammonium over a wide range of aliquot volumes and that the aliquot volume can be adjusted to optimize run times, preserve samples and increase RFU for increased sensitivity. As such, aliquot volumes for the system and process for quantifying potentially mineralizable nitrogen for an agricultural crop production are stable across a range from 20 to 100 µL. These results further illustrate that the aliquot volumes can be optimized for run time, accuracy and sample preservation over a very wide range of aliquot volumes when using the system and process disclosed herein.

Example 4

Matrix Effects on Quantification of Amino Acids and Amino Sugars in 2M KCl Soil Extracts A full factorial design with eight (8) soils and two (2) products, with three (3) replications was utilized. The products were glutamine and glucosamine at a concentration of 10 µM, and the soils had a wide range of both TN and TC values with similar concentrations of inorganic nitrogen. The aliquot volume was based on findings from Example 3 above.

The results of this experiment indicate that the system and process can accurately quanitify amino acids, amino sugars and ammonium over a wide range of soil types, soil textures and soil series. In addition, the system and process can be used to accurately quantify amino acids, amino sugars and ammonium over a wide range of soil textures, soil series, soil organic matter levels and soil total nitrogen concentrations. The potential influence of discoloration of extracts based on soil organic matter does not impact the ability of the system and process to quantify the compounds of interest.

Example 5

Comparison of 2M KCl Extract Ratios Commonly Used in Mainstream Soil-Testing Laboratories The experimental design for this example compares several extract ratios to further illustrate that the system and process is sufficient in extracting and quantifying free amino acids and amino sugars. The KCL aliquot to soil ratio is between 20:1 and 5:1.

Figure 7:
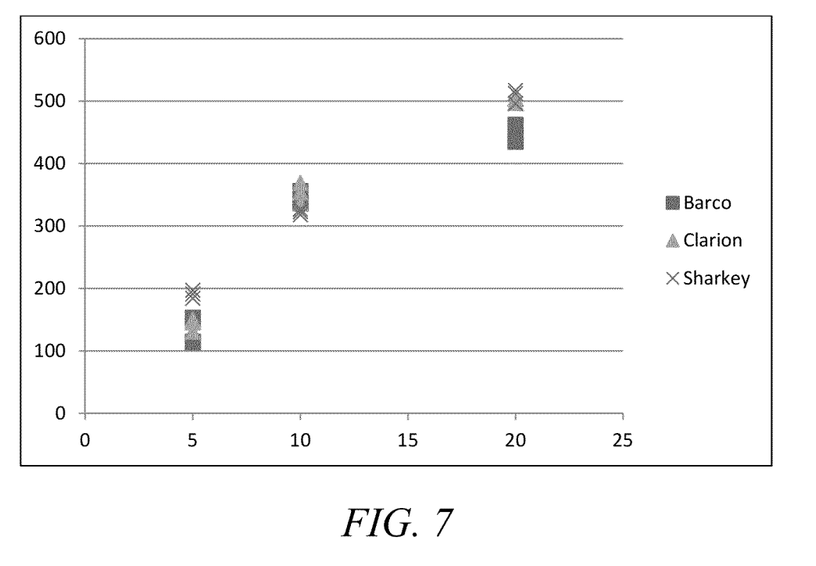
FIG. 7 graphically illustrates the relationship between extraction ratio on RFU for the three (3) soil series in accordance with Example 5 of the system and method for quantifying potentially mineralizable nitrogen for agricultural crop production disclosed herein.

FIG. 7 highlights the relationship between extraction ratio on RFU for three (3) soil series utilized in the experiment. The results of this experiment indicate that this system and process accurately quanitify amino acids, amino sugars and ammonium over a wide range of extraction ratios that are commonly used in soil test labs. In addition, dilution ratios of 5:1, 10:1 and 20:1 (KCl:soil) are effective at quantifying amino acids, amino sugars and ammonium using the system and process for quantifying potentially mineralizable nitrogen for agricultural crop production over a very wide range of extraction ratios.

Example 6

Correlation of Potentially Mineralizable N Using Fluorescence with Rice Grain Yield and N Rate to Achieve 95% RGY The nitrogen rate to achieve 90, 95, and 100% relative grain yield was determined using a regression model fit to yield response curves for each of the individual sites studied. The nitrogen rate for a given percent relative grain yield (ex. 95% relative grain yield) for a site was regressed against the soil test value for the 45 cm depth and used to develop the calibration curves illustrated in FIGS. 8 and 9. The calibration curves allow the producer to predict the nitrogen fertilizer rate required to achieve the desired relative grain yield of rice and wheat for a particular location. Multiple calibration curves (90, 95 and 100%) for percent relative grain yield allow the producer to determine which approach fits their production system the best and may change depending on nitrogen fertilizer cost and grain price. In many cases there are no statistical differences between the yields obtained from each of the three curves, but there may be numerical differences that drive the economics to either use more or less nitrogen fertilizer depending on profitability. These curves have been identified for rice.

Figure 8:
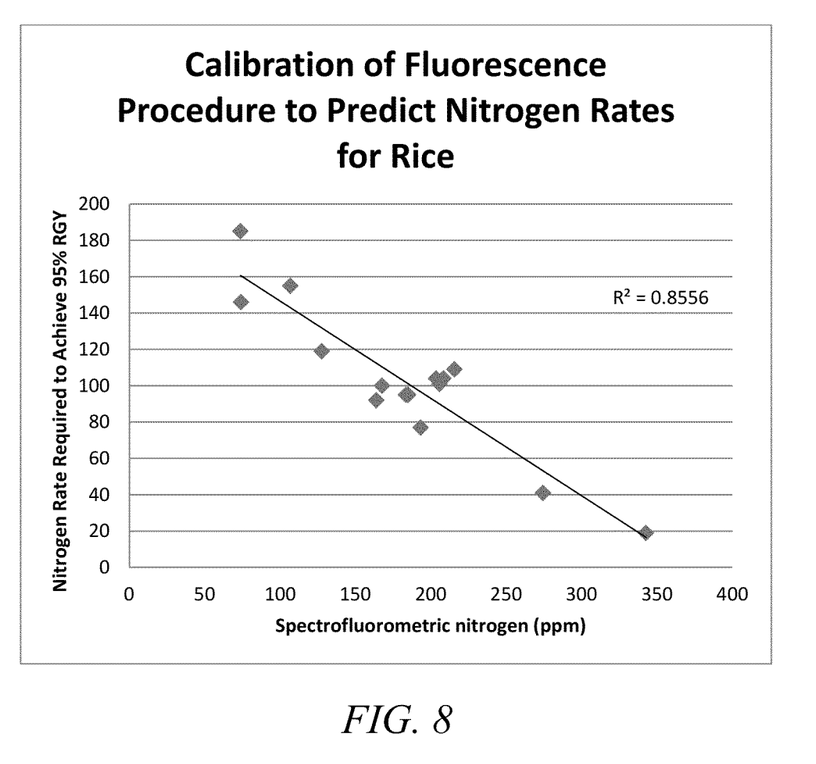
FIG. 8 graphically illustrates the relationship between the nitrogen rate required to achieve 95% RGY and the potentially mineralizable nitrogen obtained in accordance with Example 6 the system and method for quantifying potentially mineralizable nitrogen for agricultural crop production disclosed herein.
Figure 9:
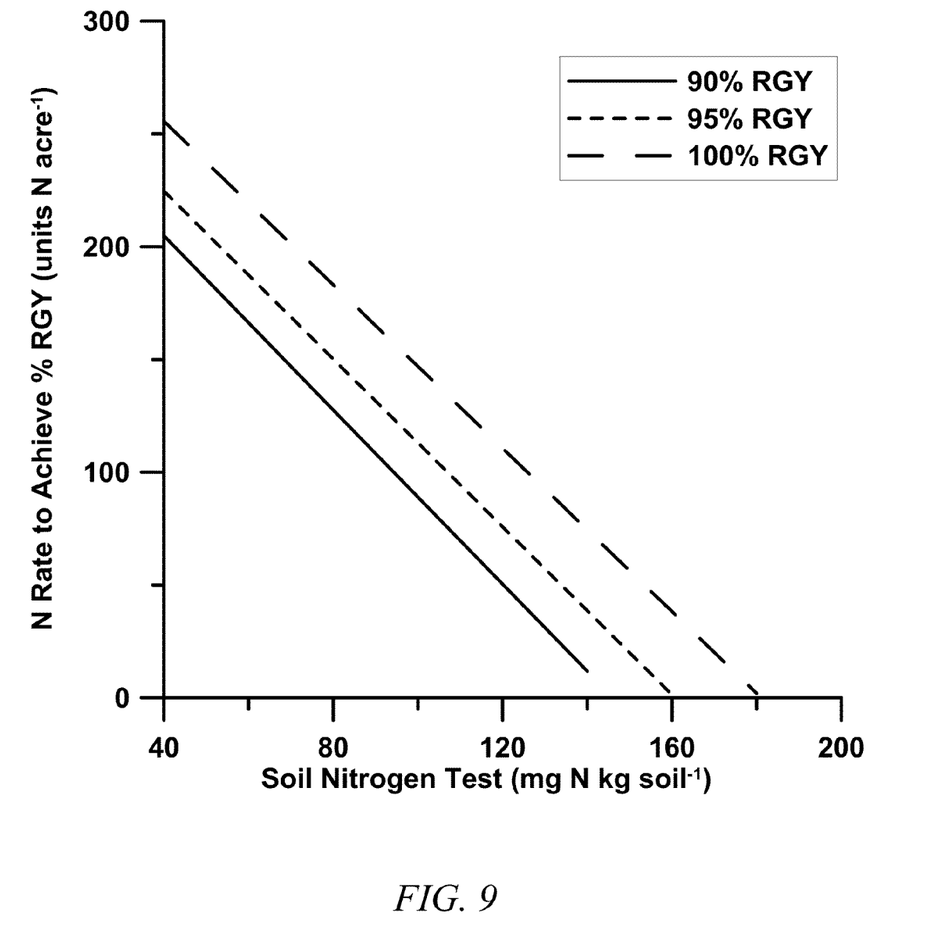
FIG. 9 is a nitrogen fertilizer calibration curve to predict nitrogen rates for rice grown on silt loam soils based on relative yield goal in accordance with Example 6 the system and method for quantifying potentially mineralizable nitrogen for agricultural crop production disclosed herein.

FIGS. 8 and 9 highlight the relationship between the nitrogen rate required to achieve 95% RGY and the potentially mineralizable nitrogen obtained using the fluorescence procedure. As can be seen, the amount of potentially mineralizable nitrogen obtained using the fluorescence system and process disclosed herein is highly and significantly correlated with nitrogen required to produce 95% RGY in rice. The fluorescence system and process described herein captures the pool of potentially mineralizable soil nitrogen that becomes available to a rice crop during the growing season and allows accurate adjustments to be made to the application of fertilizer nitrogen required to maximize rice grain yield. These results also indicate the ability to predict site-specific nitrogen fertilizer rates for rice using this system and process.

Whereas, the processes and systems have been described in relation to the drawings and claims, it should be understood that other and further modifications, apart from those shown or suggested herein, may be made within the scope of this invention.

What is claimed is:

1. A process for quantifying potentially mineralizable nitrogen for production of an agricultural crop, said process comprising the steps of:
  a. fluorometrically quantifying at least one amino acid or amino sugar content having an exposed amine group from an agricultural crop soil sample of said agricultural crop using a salt solution; wherein said amino acid or amino sugar content excludes unexposed amine groups; and
  b. quantifying a potentially mineralizable soil nitrogen content of said agricultural crop based on said amino acid or amino sugar content from said quantification of step a.

2. The process of claim 1 wherein said salt solution is potassium chloride or calcium chloride.

3. The process of claim 2 wherein said potassium chloride is 2 molar potassium chloride.

4. The process of claim 3 wherein said potassium chloride comprises an aliquot volume range between about 20 µL and about 100 µL.

5. The process of claim 1 further comprising the step of spectrofluorometrically quantifying said at least one amino acid or amino sugar content from said agricultural crop using a potassium chloride aliquot.

6. The process of claim 1 wherein said agricultural crop is produced on a sandy loam, silt loam or clay soil.

7. The process of claim 6 wherein said agricultural crop is selected from the group consisting of rice, corn, grain sorghum, cotton, wheat, pastures and hay.

8. The process of claim 1 further comprising the step of predicting at least about 90% of a maximum potential yield of said crop based on said potentially mineralizable soil nitrogen.

9. The process of claim 1 wherein a ratio of said salt solution to soil sample is between about 1:1 to about 20:1.

10. The process of claim 1 wherein said step of fluorometrically quantifying further comprising using a reagent of o-phthaldialdehyde or β-mercaptoethanol.

11. The process of claim 1 wherein said step of fluorometrically quantifying further comprising using a thiol reagent.

12. The process of claim 11 wherein said thiol reagent is selected from the group consisting of ethanethiol, 3-mercaptopropionic acid and N-acetyl-L-cysteine.

13. The process of claim 1 wherein said at least one amino acid or amino sugar content further comprises a total amino acid and amino sugar content.

14. The process of claim 13 wherein said total amino acid and amino sugar content includes said exposed amine groups selected from the group consisting of arginine, glutamine, glycine, lysine, glucosamine, mannosamine and galactosamine.

15. The process of claim 1 wherein said unexposed amine groups is proline and/or N-acetyl-glucosamine.

16. The process of claim 1 further comprising the step of determining a nitrogen fertilization rate for said crop based on said amino acid or amino sugar content of said soil sample.

17. The process of claim 16 further comprising the step of providing said nitrogen fertilization rate to achieve a predetermined yield potential for said crop.

18. The process of claim 17 further comprising the step of providing a recommended amount of nitrogen per unit area to be applied based on said nitrogen fertilization rate in order to maximize said predetermined yield potential for said crop.

19. The process of claim 16 wherein said step of determining said nitrogen fertilization rate further comprises the step of providing a mathematical model forming a yield potential response curve as a function of said nitrogen fertilization rate.

20. A process of determining a nitrogen fertilization rate for an agricultural crop, said process comprising the steps of:
  a. fluorometrically quantifying at least one amino acid or amino sugar content from of said crop using a salt solution, wherein said amino acid or amino sugar content excludes unexposed amine groups;
  b. determining a potentially mineralizable soil nitrogen content of said crop based on said amino acid or amino sugar content; and
  c. determining said nitrogen fertilization rate for said crop based on said potentially mineralizable soil nitrogen content.

21. The process of claim 20 further comprising the step of spectrofluorometrically quantifying said amino acid or amino sugar content using said salt solution, wherein said amino acid or amino sugar content excludes proline and/or N-acetyl-glucosamine.

22. The process of claim 20 wherein said agricultural crop is produced on sandy loam, silt loam or clay soil.

23. The process of claim 22 wherein said agricultural crop is selected from the group consisting of rice, corn, grain sorghum, cotton, wheat, pastures and hay.

24. The process of claim 20 wherein said at least one amino acid or amino sugar content further comprises a total amino acid and amino sugar content.

25. The process of claim 20 wherein said at least one amino acid or amino sugar content is selected from the group consisting of arginine, glutamine, glycine, lysine, glucosamine, mannosamine and galactosamine.

26. The process of claim 20 further comprising the step of predicting at least about 90% of a maximum potential yield of said crop based on said potentially mineralizable soil nitrogen.

27. The process of claim 20 further comprising the step of providing said nitrogen fertilization rate to achieve a predetermined yield potential for said crop.

28. The process of claim 27 further comprising the step of providing a recommended amount of nitrogen per unit area to be applied based on said nitrogen fertilization rate in order to maximize said predetermined yield potential for said crop.

29. The process of claim 20 wherein said step of determining said nitrogen fertilization rate further comprises the step of providing a mathematical model forming a yield potential response curve as a function of said nitrogen fertilization rate.

30. A process of providing a site-specific nitrogen fertilization rate for an agricultural crop to achieve a predetermined yield potential, said process comprising the steps of:
  a. quantifying a potentially mineralizable soil nitrogen content of said agricultural crop based on an amino acid or amino sugar content of said crop; wherein said amino acid or amino sugar content excludes unexposed amine groups; and b. providing said site-specific nitrogen fertilization rate for said crop based on said potentially mineralizable soil nitrogen content to achieve said predetermined yield potential for said crop.

31. The process of claim 30 further comprising the step of spectrofluorometrically quantifying said amino acid or amino sugar content of said crop using a salt solution, wherein said unexposed amine groups are proline and/or N-acetyl-glucosamine.

32. The process of claim 30 wherein said crop is produced on sandy loam, silt loam or clay soil.

33. The process of claim 32 wherein said agricultural crop is selected from the group consisting of rice, corn, grain sorghum, cotton, wheat, pastures and hay.

34. The process of claim 30 wherein said amino acid or amino sugar content includes arginine, glutamine, glycine, lysine, glucosamine, mannosamine, galactosamine or a combination thereof.

35. The process of claim 30 further comprising the step of predicting at least about 90% of a predetermined potential yield of said crop based on said potentially mineralizable soil nitrogen.

36. The process of claim 30 further comprising the step of providing a recommended amount of nitrogen per unit area to be applied based on said nitrogen fertilization rate in order to maximize said predetermined yield potential for said crop.

37. The process of claim 30 wherein said step of determining said nitrogen fertilization rate further comprises the step of providing a mathematical model forming a yield potential response curve as a function of said nitrogen fertilization rate.

* * * * *